(12) United States Patent
Skraly et al.

(10) Patent No.: US 6,323,010 B1
(45) Date of Patent: Nov. 27, 2001

(54) POLYHYDROXYALKANOATE BIOPOLYMER COMPOSITIONS

(75) Inventors: Frank A. Skraly, Boston; Oliver P. Peoples, Arlington, both of MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

(21) Appl. No.: 09/316,565

(22) Filed: May 21, 1999

Related U.S. Application Data

(60) Provisional application No. 60/086,396, filed on May 22, 1998.

(51) Int. Cl.$^7$ ................................. C12P 7/62; C12P 7/52

(52) U.S. Cl. ........................................... 435/135; 435/141

(58) Field of Search ..................... 435/135, 141

(56) References Cited

U.S. PATENT DOCUMENTS

| | | |
|---|---|---|
| 3,275,610 | * 9/1966 | Coty . |
| 4,477,654 | 10/1984 | Holmes et al. . |
| 5,534,432 | 7/1996 | Peoples et al. . |
| 5,798,235 | 8/1998 | Peoples et al. . |

FOREIGN PATENT DOCUMENTS

WO99/14313  3/1999 (WO) .

OTHER PUBLICATIONS

Lee et al. Applied Microbiology and Biotechnology, vol. 42, No. 6, pp. 901–909, 1995.*

Saito et al. International Journal of Biological Macromolecules, vol. 16, No. 2, pp. 99–104, 1994.*

Braunegg, et al., "Polyhydroxyalkanoates, biopolyesters from renewable resources: physiological and engineering aspects," *Journal of Biotechnology* 65:127–161 (1998).

Cao, et al., "Thermal and morphological study of fractionated poly(3–hydroxybutyric acid–co–3–hydroxyproponic acid," *Macromol. Chem. Phys.* 198:3539–3557 (1997).

Choi & Lee, "Factors affecting the economics of polyhydroxyalkanoate production by bacterial fermentation," *Appl. Microbiol. Biotechnol.* 51:13–21 (1999).

Doi, "Microbial Synthesis, Physical Properties, and Biodegradability of Polyhydroxyalkanoates," *Macromol. Symp.* 98:585–599 (1995).

Fukui, et al., "Purification and characterization of NAD-P–linked acetoacetyl–CoA reductase from *Zoogloea ramigera I–16–M*," *Biochimica Et Biophysica Acta* 917:365–371 (1987).

(List continued on next page.)

*Primary Examiner*—Francisco Prats
*Assistant Examiner*—Susan D. Coe
(74) *Attorney, Agent, or Firm*—Holland & Knight LLP

(57) ABSTRACT

Several novel PHA polymer compositions produced using biological systems include monomers such as 3-hydroxybutyrate, 3-hydroxypropionate, 2-hydroxybutyrate, 3-hydroxyvalerate, 4-hydroxybutyrate, 4-hydroxyvalerate and 5-hydroxyvalerate. These PHA compositions can readily be extended to incorporate additional monomers including, for example, 3-hydroxyhexanoate, 4-hydroxyhexanoate, 6-hydroxyhexanoate or other longer chain 3-hydroxyacids containing seven or more carbons. This can be accomplished by taking natural PHA producers and mutating through chemical or transposon mutagenesis to delete or inactivate genes encoding undesirable activities. Alternatively, the strains can be genetically engineered to express only those enzymes required for the production of the desired polymer composition. Methods for genetically engineering PHA producing microbes are widely known in the art (Huisman and Madison, 1998, Microbiology and Molecular Biology Reviews, 63: 21–53). These polymers have a variety of uses in medical, industrial and other commercial areas.

6 Claims, 2 Drawing Sheets

OTHER PUBLICATIONS

Gerngross, et al., "Overexpression and purification of the soluble polyhydroxyalkanoate synthase from *Alcaligenes eutrophus*: Evidence for a required posttranslational modification for catalytic activity," *Biochemistry* 33:9311–9320 (1994).

Hein, et al., "Biosynthesis of poly(4–hydroxybutyric acid) by recombinant strains of *Escherichia coli*," *FEMS Microbiol. Lett.* 153:411–418 (1997).

Hii & Courtright, "Induction of acyl coenzyme A synthetase and hydroxyacyl coenzyme A dehydrogenase during fatty acid degradation in Neurospora crassa.," *J. Bacteriol.* 150(2):981–983 (1982).

Hofmeister & Buckel, "(R)–lactyl–CoA dehydratase from *Clostridium propionicum*. Stereochemistry of the dehydration of (R)–2–hydroxybutyryl–CoA to crotonyl–CoA," *Eur. J. Biochem.* 206(2):547–552 (1992).

Jesudason & Marchessault, "Synthetic Poly[(R, S)–β–hydroxyalkanoates] with Butyl and Hexyl Side Chains," *Macromolecules* 27:2595–602 (1994).

Madison & Huisman, "Metabolic engineering of poly(3–hydroxyalkanoates): from DNA to plastic," *Microbiology and Molecular Biology Reviews* 63:21–53 (1999).

Peoples, et al., "Biosynthetic Thiolase from *Zoogloea ramigera*," *J. Biol. Chem.* 262:97–102 (1987).

Peoples & Sinskey, "Poly—hydroxybutyrate (PHB) biosynthesis in *Alcaligenes eutrophus* H16. Identification and characterization of the PHB polymerase gene (phbC)," *J. Biol. Chem.* 264:15298–15303 (1989).

Saito, et al., "Microbial synthesis and properties of poly(3–hydroxybutyrate–co–4–hydroxybutyrate)," *Polym. Int.* 39:169–174 (1996).

Saito, et al., "An NADP–linked Acetoacetyl CoA reductase from *Zoogloea ramigera*," *Arch. Microbiol.* 114:211–217 (1977).

Senior & Dawes, "The regulation of Poly–β–hydroxybutyrate Metabolism in *Azobacter beijerinckii*," *Biochem. J.* 134:225–228 (1973).

Shimamura, et al., "Microbial Synthesis and Characterization of Poly(3–hydroxybutyrate–co–3–hydroxypropionate)," *Macromolecules* 27:4429–4435 (1994).

Söhling & Gottschalk, "Molecular analysis of the anaerobic succinate degradation pathway in *Clostridium kluyveri*," *J. Bacteriol.* 178:871–880 (1996).

Steinbüchel & Gorenflo, "Biosynthetic and biodegradable polyesters from renewable resources: current state and prospects," *Macromol. Symp.* 123:61–66 (1997).

Steinbüchel & Valentin, "Diversity of bacterial polyhydroxyalkanoic acids," *FEMS Microbiol. Lett.* 128:219–28 (1995).

Valentin, et al., "Identification of 4–hydroxyhexanoic acid as a new constituent of biosynthetic polyhydroxyalkanoic acids from bacteria," *Appl. Microbiol. Biotechnol.* 40:710–16 (1994).

Valentin, et al., "Identification of 4–hydroxyvaleric acid as a constituent of biosynthetic polyhydroxyalkanoic acids from bacteria," *Appl. Microbiol. Biotechnol.* 36:507–14 (1992).

Valentin & Dennis., "Production of poly(3–hydroxybutyrate–co–4–hydroxybutyrate) in recombinant *Escherichia coli* grown on glucose," *J. Biotechnol.* 58:33–38 (1997).

Willadsen & Buckel, "Assay of 4–hydroxybutyryl–CoA dehydrates from *Clostridium aminobutyricum*," *FEMS Microbiol. Lett.* 70:187–192 (1990).

Williams & Peoples, "Biodegradable plastics from plants," *Chemtech* 26:38–44 (1996).

Lee, et al., "Copolymerization of gamma–valerolactone and beta–butyrolactone," *Eur. Polym. J.* 34: 117–122 (1998).

Nawrath, et al., "Targeting of the polyhydroxybutyrate biosynthetic pathway to the plastids of *Arabidopsis thaliana* results in high levels of polymer accumulation," *Proc. Natl. Acad. Sci. USA* 91:12760–64 (1994).

Yim, et al., "Synthesis of Poly–(3–hydroxybutyrate–co–3–hydroxyvalerate) by recombinant *Escherichia coli*," *Biotech. Bioengineering* 49:495–503 (1996).

* cited by examiner

POLYHYDROXYALKANOATE BIOPOLYMER COMPOSITIONS

This application claims priority to U.S. Ser. No. 60/086,396 filed May 22, 1998.

BACKGROUND TO THE INVENTION

Numerous microorganisms have the ability to accumulate intracellular reserves of PHA polymers. Poly [(R)-3-hydroxyalkanoates] (PHAs) are biodegradable and biocompatible thermoplastic materials, produced from renewable resources, with a broad range of industrial and biomedical applications (Williams and Peoples, 1996, CHEMTECH 26, 38–44). Around 100 different monomers have been incorporated into PHA polymers, as reported in the literature (Steinbüchel and Valentin, 1995, FEMS Microbiol. Lett. 128; 219–228) and the biology and genetics of their metabolism has recently been reviewed (Huisman and Madison, 1998, Microbiology and Molecular Biology Reviews, 63: 21–53).

To date, PHAs have seen limited commercial availability, with only the copolymer poly(3-hydroxybutyrate-co-3-hydroxyvalerate) (PHBV) being available in development quantities. This copolymer has been produced by fermentation of the bacterium Ralstonia eutropha. Fermentation and recovery processes for other PHA types have also been developed using a range of bacteria including Azotobacter, Alcaligenes latus, Comamonas testosterone and genetically engineered E. coli and Klebsiella and have recently been reviewed (Braunegg et al., 1998, Journal of Biotechnology 65: 127–161; Choi and Lee, 1999, Appl. Microbiol. Biotechnol. 51: 13–21). More traditional polymer synthesis approaches have also been examined, including direct condensation and ring-opening polymerization of the corresponding lactones (Jesudason and Marchessault, 1994, Macromolecules 27: 2595–2602).

Synthesis of PHA polymers containing the monomer 4-hydroxybutyrate (PHB4HB, Doi, Y. 1995, Macromol. Symp. 98, 585–599) or 4-hydroxyvalerate and 4-hydroxyhexanoate containing PHA polyesters have been described (Valentin et al., 1992, Appl. Microbiol. Biotechnol. 36, 507–514 and Valentin et al., 1994, Appl. Microbiol. Biotechnol. 40, 710–716). These polyesters have been manufactured using methods similar to that originally described for PHBV in which the microorganisms are fed a relatively expensive non-carbohydrate feedstock in order to force the incorporation of the monomer into the PHA polyester. The PHB4HB copolymers can be produced with a range of monomer compositions which again provides a range of polymer (Saito, Y, Nakamura, S., Hiramitsu, M. and Doi, Y., 1996, Polym. Int. 39: 169).

PHA copolymers of 3-hydroxybutyrate-co-3-hydroxypropionate have also been described (Shimamura et. al., 1994, Macromolecules 27: 4429–4435; Cao et. al., 1997, Macromol. Chem. Phys. 198: 3539–3557). The highest level of 3-hydroxypropionate incorporated into these copolymers 88 mol % (Shimamura et. al., 1994, Macromolecules 27: 4429–4435).

PHA terpolymers containing 4-hydroxyvalerate have been produced by feeding a genetically engineered Pseudomonas putida strain on 4-hydroxyvalerate or levulinic acid which resulted in a three component PHA, Poly(3-hydroxybutyrate-co-3-hydroxyvalerate-4-hydroxyvalerate) (Valentin et. al., 1992, Appl. Microbiol. Biotechnol. 36: 507–514; Steinbüchel and Gorenflo, 1997, Macromol. Symp. 123: 61–66). It is desirable to develop biological systems to produce two component polymers comprising 4-hydroxyvalerate or poly(4-hydroxyvalerate) homopolymer. The results of Steinbüchel and Gorenflo (1997, Macromol. Symp. 123: 61–66) indicate that Pseudomonas putida has the ability to convert levulinic acid to 4-hydroxyvalerate.

Hein et al. (1997) attempted to synthesize poly-4HV using transgenic Escherichia coli strain XL1-Blue but were unsuccessful. These cells carried a plasmid which permitted expression of the A. eutrophus PHA synthase and the Clostridium kluyveri 4-hydroxybutyryl-CoA transferase genes. When the transgenic E. coli were fed 4HV, □-valerolactone, or levulinic acid, they produced only a small amount of PHB homopolymer.

It is clearly desirable for industrial reasons to be able to produce a range of defined PHA homopolymer, copolyer and terpolymer compositions. To accomplish this, it is desirable to be able to control the availability of the individual enzymes in the corresponding PHA biosynthetic pathways.

It is therefore an object of the present invention to provide a range of defined PHA homopolymer, copolyer and terpolymer compositions.

It is another object of the present invention to provide a method and materials to control the availability of the individual enzymes in the corresponding PHA biosynthetic pathways.

SUMMARY OF THE INVENTION

Several novel PHA polymer compositions produced using biological systems include monomers such as 3-hydroxybutyrate, 3-hydroxypropionate, 2-hydroxybutyrate, 3-hydroxyvalerate, 4-hydroxybutyrate, 4-hydroxyvalerate and 5-hydroxyvalerate. These PHA compositions can readily be extended to incorporate additional monomers including, for example, 3-hydroxyhexanoate, 4-hydroxyhexanoate, 6-hydroxyhexanoate or other longer chain 3-hydroxyacids containing seven or more carbons. This can be accomplished by taking natural PHA producers and mutating through chemical or transposon mutagenesis to delete or inactivate genes encoding undesirable activities. Alternatively, the strains can be genetically engineered to express only those enzymes required for the production of the desired polymer composition. Methods for genetically engineering PHA producing microbes are widely known in the art (Huisman and Madison, 1998, Microbiology and Molecular Biology Reviews, 63: 21–53). These polymers have a variety of uses in medical, industrial and other commercial areas.

DETAILED DESCRIPTION OF THE INVENTION

Figure 1:
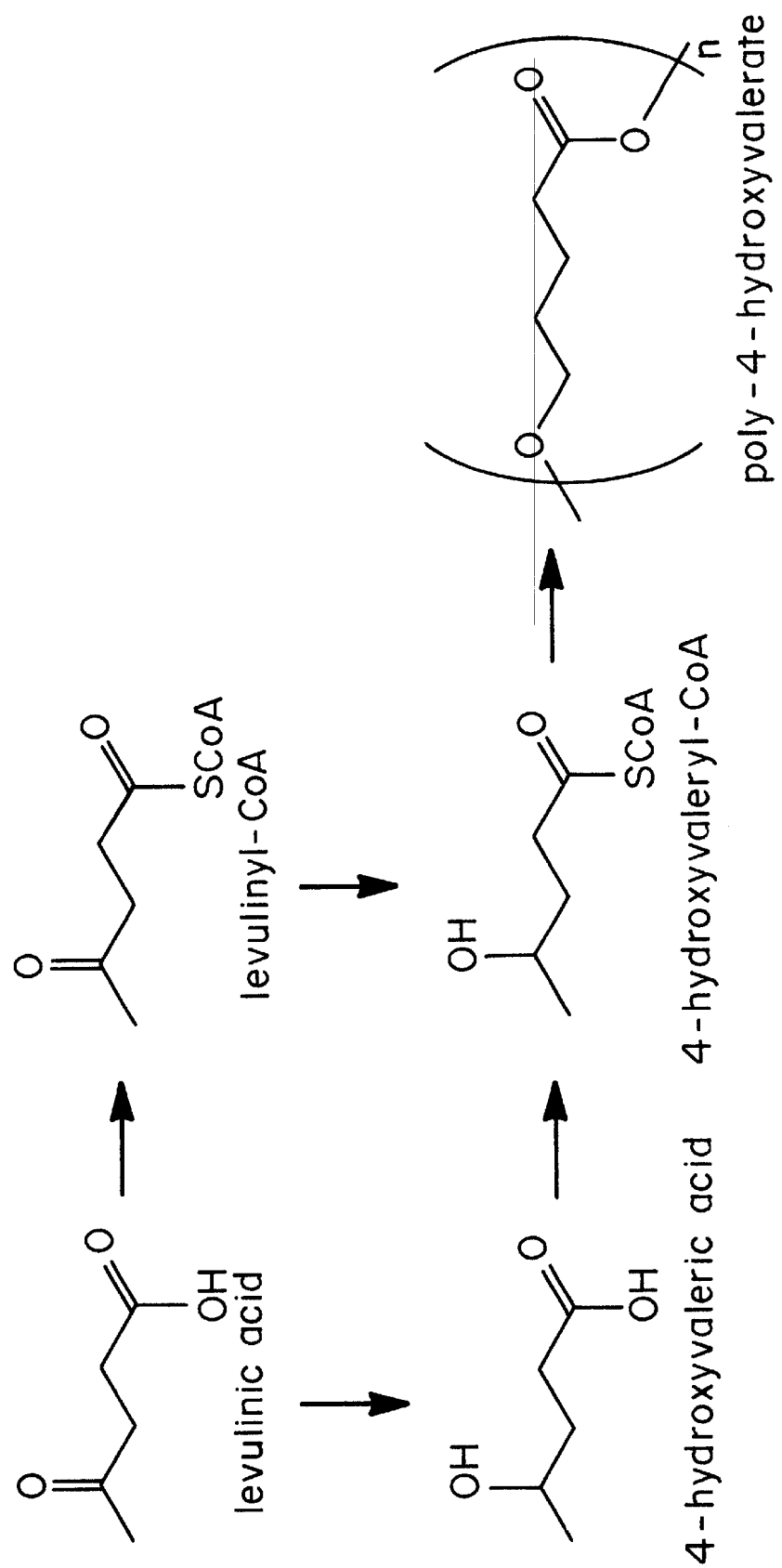
FIG. 1 is a schematic of the pathway from levulinic acid to poly-4-hydroxyvalerate.

Several novel PHA polymer compositions have been produced using biological systems to incorporate monomers such as 3-hydroxybutyrate, 3-hydroxypropionate, 2-hydroxybutyrate, 3-hydroxyvalerate, 4-hydroxybutyrate, 4-hydroxyvalerate and 5-hydroxyvalerate. These PHA compositions can readily be extended to incorporate additional monomers including, for example, 3-hydroxyhexanoate, 4-hydroxyhexanoate, 6-hydroxyhexanoate or other longer chain 3-hydroxyacids containing seven or more carbons. Techniques and procedures to engineer transgenic organisms that synthesize PHAs containing one or more of these monomers either as sole constituent or as co-monomer have been developed. In these systems the transgenic organism is either a bacterium eg. *Escherichia Coli, K. pneumoniae, Ralstonia eutropha* (formerly *Alcaligenes eutrophus*), *Alcaligenes latus* or other microorganisms able to synthesize PHAs, or a higher plant or plant component, such as the seed of an oil crop (Brassica, sunflower, soybean, corn, safflower, flax, palm or coconut or starch accumulating plants (potato, tapioca, cassava).

It is crucial for efficient PHA synthesis in recombinant *E. coli* strains that the expression of all the genes involved in the pathway be adequate. To this end, the genes of interest can be expressed from extrachromosomal DNA molecules such as plasmids, which intrinsically results in a copy number effect and consequently high expression levels, or, more preferably, they can be expressed from the chromosome. For large scale fermentations of commodity type products it is generally known that plasmid-based systems are unsatisfactory due to the extra burden of maintaining the plasmids and the problems of stable expression. These drawbacks can be overcome using, chromosomally encoded enzymes by improving the transcriptional and translational signals preceding the gene of interest such that expression is sufficient and stable.

The biological systems must express one or more enzymes as required to convert the monomers into polymers. Suitable substrates include 3-hydroxybutyrate, 3-hydroxypropionate, 2-hydroxybutyrate, 3-hydroxyvalerate, 4-hydroxybutyrate, 4-hydroxyvalerate, 5-hydroxyvalerate, 3-hydroxyhexanoate, 4-hydroxyhexanoate, 6-hydroxyhexanoate and other longer chain 3-hydroxyacids containing seven or more carbons. These enzymes include polyhydroxyalkanoate synthase, acyl-CoA transferase and hydroxyacyl CoA transferase, and hydroxyacyl CoA synthetase. These enzymes can be used with these substrates to produce in a biological system such as bacteria, yeast, fungi, or plants, polymer such as poly(3-hydroxybutyrate-co-4-hydroxyvalerate), poly(4-hydroxyvalerate), poly(3-hydroxypropionate-co-5-hydroxyvalerate), poly(2-hydroxybutyrate), poly(2-hydroxybutyrate-co-3-hydroxybutyrate), and poly(3-hydroxypropionate).

Genes encoding the required enzymes can be acquired from multiple sources. U.S. Pat. Nos. 5,798,235 and 5,534,432 to Peoples, et al., describe polyhydroxyalkanoate synthetase, reductase and thiolase. A 4-hydroxybutyryl CoA transferase gene from *C. aminobutyricum* is described by Willadsen and Buckel, FEMS Microbiol. Lett. (1990) 70: 187–192) or from *C. kluyveri* is described by Söhling and Gottschalk, 1996, J. Bacteriol. 178, 871–880). An acyl coenzyme A synthetase from *Neurospora crassa* is described by Hii and Courtright, J. Bacteriol. 1982. 150(2): 981–983. A hydroxyacyl transferase from Clostridium is described by Hofmeister and Bucker, Eur. J. Biochem. 1992, 206(2), 547–552.

It is important for efficient PHA production that strains do not lose the capability to synthesize the biopolymer for the duration of the inoculum train and the production run. Loss of any of the pha genes results in loss of product. Both are undesirable and stable propagation of the strain is therefore required. Merely integrating the gene encoding the transferase or synthase may not result in significant polymer production. Enzyme expression can be enhanced through alteration of the promoter region or mutagenesis or other known techniques, followed by screening for polymer production. Growth and morphology of these recombinant PHA producers is not compromised by the presence of pha genes on the chromosome.

The present invention will be further understood by reference to the following non-limiting examples.

EXAMPLE 1

Poly(3HB-co-4HV) from 4-hydroxyvalerate and Glucose in *E. coli*.

Construction of pFS16

The plasmid pTrcN is a derivative of pTrc99a (Pharmacia; Uppsala, Sweden); the modification that distinguishes pTrcN is the removal of the NcoI restriction site by digestion with NcoI, treatment with T4 DNA polymerase, and self-ligation. The orfZ gene encoding the 4-hydroxybutyryl-CoA transferase from *Clostridium kluyveri* was amplified using the polymerase chain reaction (PCR) and a kit from Perkin Elmer (Foster City, Calif.) using plasmid pCK3 (Söhling and Gottschalk, 1996, J. Bacteriol. 178: 871–880) as the target DNA and the following oligonucleotide primers:

5'-TCCCCTAGGATTCAGGAGGTTTTTATGGAGTG GGAAGAGATATATAAAG -3'

(orfZ 5' AvrII)

5'-CCTTAAGTCGACAAATTCTAAAATCTCTTTTA AATTC-3'

(orfZ 3' SalI)

The resulting PCR product was digested with AvrII and SalI and ligated to pTrcN that had been digested with XbaI (which is compatible with AvrII) and SalI to form plasmid pFS16 such that the 4-hydroxybutyryl-CoA transferase can be expressed from the IPTG (isopropyl-β-D-glucopyranoside)—inducible trcpromoter.

Construction of pFS30.

The plasmid pFS30 was derived from pFS16 by adding the *Ralstonia eutropha* PHA synthase (phaC) gene (Peoples and Sinskey, 1989. J. Biol. Chem. 264:15298–15303) which had been modified by the addition of a strong *E. coli* ribosome binding site as described by (Gerngross et. al., 1994. Biochemistry 33: 9311–9320). The plasmid pAeT414 was digested with XmaI and StuI so that the *R. eutropha* promoter and the structural phaC gene were present on one fragment. pFS16 was cut with BamHI, treated with T4 DNA polymerase to create blunt ends, then digested with XmaI. The two DNA fragments thus obtained were ligated together to form pFS30. In this construct the PHB synthase and 4-hydroxybutyryl-CoA transferase are expressed from the *A. eutrophus phbC promoter (Peoples and Sinskey,* 1989. J. Biol. Chem. 264:15298–15303). Other suitable plasmids expressing PHB synthase and 4-hydroxybutyryl-CoA transferase have been described (Hein et. al., 1997, FEMS Microbiol. Lett. 153: 411–418; Valentin and Dennis, 1997, J. Biotechnol. 58 :33–38).

*E. coli* MBX769 has a PHA synthase integrated into its chromosome. This strain is capable of synthesizing, poly(3-hydroxybutyrate) (PUB) from glucose with no extrachromosomal genes present. MBX769 is also deficient in fadR, the repressor of the fatty-acid-degradation pathway and effector of many other cellular functions, it is deficient in rpoS, a regulator of stationary-phase gene expression, and it is deficient in atoA, one subunit of the acetoacetyl-CoA transferase. MBX769 also expresses atoC, a positive regulator of the acetoacetate system, constitutively.

Figure 2:
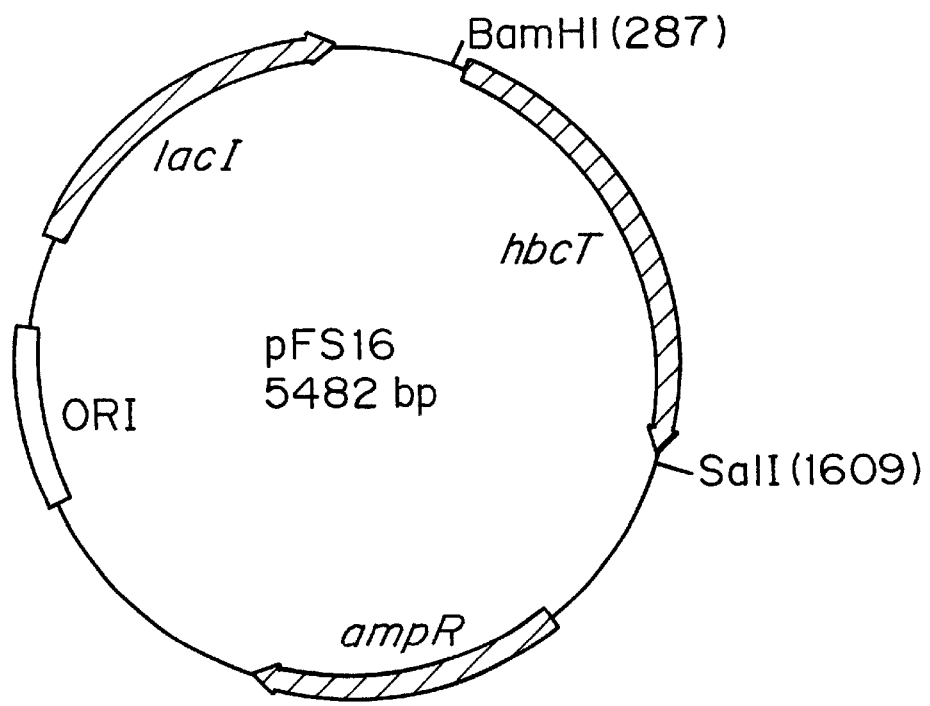
FIG. 2 is a schematic of a construct of plasmid pFS16, which includes the lacI (inducer) gene, ampicillin resistance gene, and hbcT gene.
Figure 3:
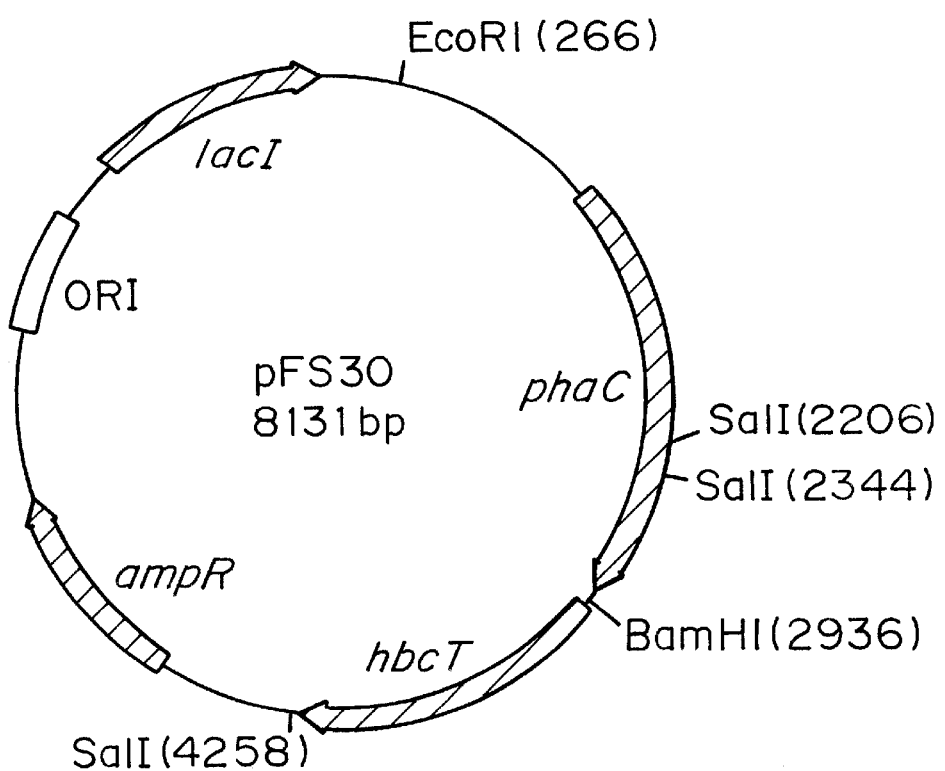
FIG. 3 is a schematic of a construct of plasmid pFS30, which includes the lacI (inducer) gene, ampicillin resistance gene, polyhydroxyalkanoate polymerase (phaC) gene, and hbcT gene.

*E. coli* MBX769 carrying the plasmid pFS16 (FIG. 2), which permitted the expression of the *Clostridium kluyveri* 4-hydroxybutyryl-CoA transferase, was precultured at 37° C. in 100 mL of LB medium containing 100 μg/mL sodium ampicillin in a 250-mL Erlenmeyer flask with shaking at 200 rpm. The cells were centrifuged at 5000 g for 10 minutes to remove them from the LB medium after 16 hours, and they were resuspended in 100 mL of a medium containing, per liter: 4.1 or 12.4 g sodium 4-hydroxyvalerate (4HV); 5 g/L sodium 4-hydroxybutyrate (4HB); 2 g glucose; 2.5 g LB broth powder (Difco; Detroit, Mich.); 50 mmol potassium phosphate, pH 7; 100 μg/mL sodium ampicillin; and 0.1 mmol isopropyl-β-D-thiogalactopyranoside (IPTG). The sodium 4-hydroxyvalerate was obtained by saponification of γ-valerolactone in a solution of sodium hydroxide. The cells were incubated in this medium for 3 days with shaking at 200 rpm at 32° C. in the same flask in which they had been precultured. When 4.1 g/L sodium 4-hydroxyvalerate was present initially, the cells accumulated a polymer to 52.6% of the dry cell weight that consisted of 63.4% 3HB units and 36.6% 4HB units but no 4HV units.

When 12.4 g/L sodium 4HV was present initially, the cells accumulated a polymer to 45.9% of the dry cell weight that consisted of 95.5% 3HB units and 4.5% 4HV units but no detectable 4HB units. The identity of the PHB-co-4HV polymer was verified by nuclear magnetic resonance (NMR) analysis of the solid product obtained by chloroform extraction of whole cells followed by filtration, ethanol precipitation of the polymer from the filtrate, and washing of the polymer with water. It was also verified by gas chromatographic (GC) analysis, which was carried out as follows. Extracted polymer (1–20 mg) or lyophilized whole cells (15–50 mg) were incubated in 3 mL of a propanolysis solution consisting of 50% 1,2-dichloroethane, 40% 1-propanol, and 10% concentrated hydrochloric acid at 100° C. for 5 hours. The water-soluble components of the resulting mixture were removed by extraction with 3 mL water. The organic phase (1 μL at a split ratio of 1:50 at an overall flow rate of 2 mL/min) was analyzed on an SPB-1 fused silica capillary GC column (30 m; 0.32 mm ID; 0.25 μm film; Supelco; Bellefonte, Pa.) with the following temperature profile: 80° C., 2 min; 10° C. per min to 250° C.; 250° C., 2 min. The standard used to test for the presence of 4HV units in the polymer was γ-valerolactone, which, like 4-hydroxyvaleric acid, forms propyl 4-hydroxyvalerate upon propanolysis. The standard used to test for 3HB units in the polymer was PHB.

EXAMPLE 2

Poly(4HV) from 4-hydroxyvalerate in *E. coli*

*Escherichia coli* MBX1177 is not capable of synthesizing poly(3-hydroxybutyrate) (PHB) from glucose. MBX1177 is a spontaneous mutant of strain DH5□ that is able to use 4-hydroxybutyric acid as a carbon source. MBX1177 carrying the plasmid pFS30 (FIG. 2), which permitted the expression of the *Clostridium kluyveri* 4HB-CoA transferase and the *Ralstonia eutropha* PHA synthase, was precultured at 37° C. in 100 mL of LB medium containing 100 μg/mL sodium ampicillin.

The cells were centrifuged at 5000 g for 10 minutes to remove them from the LB medium after 16 hours, and they were resuspended in 100 mL of a medium containing, per liter: 5 g sodium 4-hydroxyvalerate (4HV); 2 g glucose; 2.5 g LB broth powder; 100 mmol potassium phosphate, pH 7; 100 μg/mL sodium ampicillin; and 0.1 mmol IPTG. The cells were incubated in this medium for 3 days with shaking at 200 rpm at 30° C. in the same flask in which they had been precultured.

The cells accumulated a polymer to 0.25% of the dry cell weight that consisted of 100% 4HV units. The identity of the poly(4HV) polymer was verified by GC analysis of whole cells that had been washed with water and propanolyzed in a mixture of 50% 1,2-dichloroethane, 40% 1-propanol, and 10% concentrated hydrochloric acid at 100° C. for 5 hours, with γ-valerolactone as the standard.

EXAMPLE 3

Poly(3HB-co-2HB) from 2-hydroxybutyrate and Glucose in *E. coli*

*E. coli* MBX769 carrying the plasmid pFS16 was precultured at 37° C. in 100 mL of LB medium containing 100 μg/mL sodium ampicillin in a 250-mL Erlenmeyer flask with shaking at 200 rpm. The cells were centrifuged at 5000 g for 10 minutes to remove them from the LB medium after 16 hours, and they were resuspended in 100 mL of a medium containing, per liter: 5 g sodium 2-hydroxybutyrate (2HB); 2 g glucose; 2.5 g LB broth powder; 50 mmol potassium phosphate, pH 7; 100 μg/mL sodium ampicillin; and 0.1 mmol IPTG. The cells were incubated in this medium for 3 days with shaking at 150 rpm at 33° C. in the same flask in which they had been precultured. The cells accumulated a polymer to 19.0% of the dry cell weight that consisted of 99.7% 3HB units and 0.3% 2HB units. The identity of the poly(3HB-co-2HB) polymer was verified by GC analysis of the solid product obtained by chloroform extraction of whole cells followed by filtration, ethanol precipitation of the polymer from the filtrate, and washing of the polymer with water. It was also verified by GC analysis of whole cells that had been washed with water and propanolyzed in a mixture of 50% 1,2-dichloroethane, 40% 1-propanol, and 10% concentrated hydrochloric acid at 100° C. for 5 hours, with PHB and sodium 2-hydroxybutyrate as the standards.

EXAMPLE 4

Poly(2HB) from 2-hydroxybutyrate in *E. coli*

*Escherichia coli* MBX184 is not capable of synthesizing poly(3-hydroxybutyrate) (PHB) from glucose. MBX184 is deficient in fadR and expresses atoC constitutively.

MBX184 carrying the plasmid pFS30 was precultured at 37° C. in 100 mL of LB medium containing 100 μg/mL sodium ampicillin. The cells were centrifuged at 5000 g for 10 minutes to remove them from the LB medium after 16 hours, and they were resuspended in 100 mL of a medium containing, per liter: 5 g sodium 2-hydroxybutyrate (2HB); 2 g glucose; 2.5 g LB broth powder; 50 mmol potassium phosphate, pH 7; 100 μg/mL sodium ampicillin; and 0.1 mmol IPTG. The cells were incubated in this medium for 3 days with shaking at 150 rpm at 33° C. in the same flask in which they had been precultured.

The cells accumulated a polymer to 1.0% of the dry cell weight that consisted of 100% 2HB units. The identity of the poly(2HB) polymer was verified by GC analysis of whole cells that had been washed with water and propanolyzed in a mixture of 50% 1,2-dichloroethane, 40% 1-propanol, and 10% concentrated hydrochloric acid at 100° C. for 5 hours, with sodium 2-hydroxybutyrate as the standard.

EXAMPLE 5

Poly-3HP and poly-3HP-co-5HV from 1,3-propanediol and from 1,5-pentanediol.

*Escherichia coli* MBX184 carrying the plasmid pFS30 was precultured at 37° C. in 100 mL of LB medium containing 100 μg/mL sodium ampicillin. The cells were centrifuged at 5000 g for 10 minutes to remove them from the LB medium after 16 hours, and they were resuspended in 100 mL of a medium containing, per liter: 10 g 1,3-propanediol (1,3-PD) or 1,5-pentanediol (1,5-PD); 2 g glucose; 2.5 g LB broth powder; 50 mmol potassium phosphate, pH 7; 100 μg/mL sodium ampicillin; and 0.1 mmol IPTG. The cells were incubated in this medium for 3 days with shaking at 200 rpm at 30° C. in the same flask in which they had been precultured. When the diol substrate was 1,3-PD, the cells accumulated a polymer to 7.0% of the dry cell weight that consisted entirely of 3HP units. When the substrate was 1,5-PD, the cells accumulated a polymer to 22.1 % of the dry cell weight that consisted of greater than 90% 3-hydroxypropionate units and less than 10% 5-hydroxyvalerate units. The identity of the poly(3-hydroxypropionate) polymer was verified by NMR analysis of the solid product obtained by sodium hypochlorite extraction of whole cells followed by centrifugation and washing of the polymer with water. The identity of both polymers was verified by GC analysis of sodium hypochlorite-extracted polymer that was propanolyzed in a mixture of 50% 1,2-dichloroethane, 40% 1-propanol, and 10% concentrated hydrochloric acid at 100° C. for 5 hours, with β-propiolactone and δ-valerolactone as the standards.

EXAMPLE 6

Poly-5HV from 5-hydroxyvaleric acid

*Escherichia coli* MBX1177 carrying the plasmid pFS30 was precultured at 37° C. in 50 mL of LB medium containing 100 μg/mL sodium ampicillin. The cells were centrifuged at 5000 g for 10 minutes to remove them from the LB medium after 8 hours, and they were resuspended in 100 mL of a medium containing, per liter: 10 g sodium 5-hydroxyvalerate (5HV); 5 g glucose; 2.5 g LB broth powder; 50 mmol potassium phosphate, pH 7; 100 μg/mL sodium ampicillin; and 0.1 mmol IPTG. The sodium 5HV was obtained by saponification of d-valerolactone. The cells were incubated in this medium for 3 days with shaking at 200 rpm at 30° C. in the same flask in which they had been precultured. GC analysis was conducted with lyophilized whole cells that were butanolyzed in a mixture of 90% 1-butanol and 10% concentrated hydrochloric acid at 110° C. for 5 hours; the standard was sodium 5-hydroxyvalerate. This analysis showed that the cells had accumulated poly (5HV) to 13.9% of the dry cell weight. The identity of the poly(5-hydroxyvalerate) polymer was verified by NMR analysis of the solid product obtained by 1,2-dichloroethane extraction of whole cells followed by centrifugation and washing of the polymer with water.

Modifications and variations are intended to come within the scope of the appended claims.

---

---

We claim:

1. A method for making polymers in a biological system comprising
   providing one or more substrates which comprise 2-hydroxybutyric acid,
   wherein the biological system is genetically engineered to express one or more enzymes selected from the group consisting of polyhydroxyalkanoate synthase, acyl-CoA transferase, hydroxyacyl CoA transferase, and hydroxyacyl CoA synthetase, such that a polymer comprising 2-hydroxybutyric acid accumulates.

2. The method of claim 1 wherein the biological system expresses one or more heterologous genes encoding the enzymes.

3. The method of claim 1 for making a copolymer of 2-hydroxybutyrate and at least one monomer selected from the group consisting of 3-hydroxybutyrate, 3-hydroxypropionate, 4-hydroxyvalerate, and 4-hydroxybutyrate further comprising providing in addition to 2-hydroxybutyrate, at least one monomer selected from the group consisting of (R)-3-hydroxybutyrate, 3-hydroxypropionate, 4-hydroxyvalerate, and 4-hydroxybutyrate, and incubating the monomers with 4-hydroxybutyrate CoA transferase.

4. The method of claim 1 wherein the biological system is genetically engineered to prevent expression of enzymes so that only enzymes required for the production of the desired polymer composition are expressed.

5. The method of claim 4 wherein the biological system is engineered by mutation.

6. The method of claim 1 wherein the biological system is genetically engineered to enhance enzyme expression or activity.

* * * * *

UNITED STATES PATENT AND TRADEMARK OFFICE
CERTIFICATE OF CORRECTION

PATENT NO. : 6,323,010 B1  
APPLICATION NO. : 09/316565  
DATED : November 27, 2001  
INVENTOR(S) : Frank A. Skraly and Oliver P. Peoples Page 1 of 1

It is certified that error appears in the above-identified patent and that said Letters Patent is hereby corrected as shown below:

In the Drawings Sheet 1 of 2  
Figure 1, the structure  
"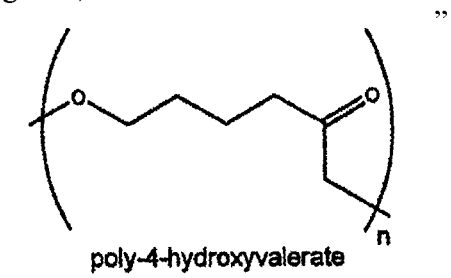"

should be

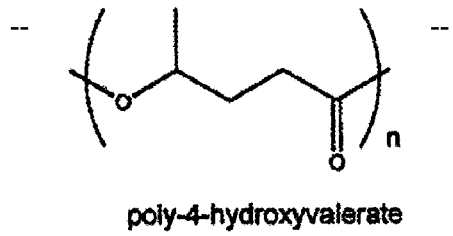

Signed and Sealed this

Fourteenth Day of October, 2008

JON W. DUDAS  
*Director of the United States Patent and Trademark Office*

SEQUENCE LISTING

```
<160> NUMBER OF SEQ ID NOS: 2

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence:
      Primer- orfZ 5' AvrII
<220> FEATURE:
<221> NAME/KEY: misc_feature
<222> LOCATION: (1)..(49)
<223> OTHER INFORMATION: oligonucleotide primer

<400> SEQUENCE: 1
tcccctagga ttcaggaggt ttttatggag tgggaagaga tatataaag            49

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:
      Primer- orfZ 3' SalI
<220> FEATURE:
<221> NAME/KEY: misc_feature
<222> LOCATION: (1)..(38)
<223> OTHER INFORMATION: oligonucleotide primer

<400> SEQUENCE: 2
ccttaagtcg acaaattcta aaatctcttt ttaaattc                        38
```